United States Patent [19]

Drayna et al.

[11] Patent Number: 5,753,438

[45] Date of Patent: May 19, 1998

[54] METHOD TO DIAGNOSE HEREDITARY HEMOCHROMATOSIS

[75] Inventors: Dennis T. Drayna, San Mateo; John N. Feder, Mountain View; Andreas Gnirke, San Carlos; Bruce E. Kimmel; Winston J. Thomas, both of San Mateo; Roger K. Wolff, San Francisco, all of Calif.

[73] Assignee: Mercator Genetics, Inc., Menlo Park, Calif.

[21] Appl. No.: 436,074

[22] Filed: May 8, 1995

[51] Int. Cl.$^6$ .............................. C12Q 1/68; C12P 19/34; C07H 21/04

[52] U.S. Cl. .......................... 435/6; 435/91.2; 435/810; 536/24.33

[58] Field of Search ............................ 435/6, 91.1, 91.2, 435/810, 270, 183; 536/24.33, 24.31; 935/76, 77

[56] References Cited

PUBLICATIONS

Olynyk, et al., "Hepatic Iron Concentration as a predictor of response to interferon alpha therapy in chronic hepatitis C", Gastroenterology 108:1104–1109, Jan. 1995.

Gyapay, G., et al., "The 1993–94 Genethon Human Genetic Linkage Map", Nature Genetics, vol. 7, pp. 246–339, Jun. 1994.

Stone, C., et al., "Isolation of CA Dinucleotide Repeats Close to D6S105; Linkage Disequilibrium with Haemochromatosis", Human Molecular Genetics, vol. 3, No. 11, pp. 2043–2046, Nov. 1994.

Pearson, W.R., et al., "Improved Tools for Biological Sequence Comparison", Proc. Natl. Acad. Sci. USA, vol. 85, pp. 2444–2448, Apr. 1988.

Worwood, M., et al., "Alleles at D6S265 and D6S105 Define a Haemochromatosis–Specific Genotype", British Journal of Haematology, vol. 86, pp. 863–866, 1994.

Niederau, C., et al., "Disease Associations: Which Factors Determine the Development of Liver Cancer in Hereditary Hemochromatosis?", Cancer Biotechnology Weekly, p. 415, 11 Mar. 1996.

Piperno, A., et al., "Liver Damage in Italian Patients with Hereditary Hemochromatosis is Highly Influenced by Hepatitis B and C Virus Infection", Journal of Hepatology, vol. 16, No. 3, pp. 364–368, 1992.

Rubin, R.B., et al., "Iron and Chronic Viral Hepatitis: Emerging Evidence for an Important Interaction", Digestive Diseases, vol. 13, No. 4, pp. 223–238, Jul. 1995.

Arber, N., et al., "Elevated Serum Iron Predicts Poor Response to Interferon Treatment in Patients with Chronic HCV Infection", Digestive Diseases and Sciences, vol. 40, No. 11, pp. 2431–2433, Nov. 1995.

Wilbur, W.J., et al., "Rapid Similarity Searches of Nucleic Acid and Protein Data Banks", Proc. Natl., Acad. Sci. USA, vol. 80, pp. 726–730, Feb. 1983.

Beutler, E., et al., "A Strategy for Cloning the Hereditary Hemochromatosis Gene", Blood Cells, Molecules, and Diseases, vol. 21, No. 21, pp. 207–216, 15 Nov. 1995.

Burt, M.J., et al., "A 4.5–Megabase YAC Contig and Physical Map Over the Hemochromatosis Gene Region", Genomics, vol. 33, pp. 153–158, Feb. 1996.

Totaro, A., et al., "Hereditary Hemochromatosis: Generation of a Transcription Map Within a Refined and Extended Map of the HLA Class I Region", Genomics, vol. 31, pp. 319–326, 1996.

Calandro, L.M., et al., "Characterization of a Recombinant That Locates the Hereditary Hemochromatosis Gene Telomeric to HLA–F", Human Genetics, vol. 96, pp. 339–342, 1995.

Gasparini, P., et al., "Linkage Analysis of 6p21 Polymorphic Markers and the Hereditary Hemochromatosis: Localization of the Gene Centromeric to HLA–F", Human Molecular Genetics, vol. 2, No. 5, pp. 571–576, May 1993.

Jazwinska, E.C., et al., "Localization of the Hemochromatosis Gene Close to D6S105", Am. J. Hum. Genet., vol. 53, pp. 347–352, 1993.

Totaro, A., et al., "New Markers and Polymorphisms in the Hereditary Hemochromatosis (HFE) Gene Region", Miami Biotechnology Short Report: Conference Proceedings Mol. Biol. Hum. Diseases, vol. 5, p. 53, Nov. 1994.

Totaro, A., et al., "New Polymorphisms and Markers in the HLA Class I Region: Relevance to Hereditary Hemochromatosis (HFE)", Human Genetics, vol. 95, No. 4, pp. 429–434, Apr. 1995.

Yaouanq, J., et al., "Anonymous Marker Loci Within 400 kb of HLA–A Generate Haplotypes in Linkage Disequilibrium with the Hemochromatosis Gene (HFE)", Am. J. Hum. Genet., vol. 54, pp. 252–263, 1994.

Finch, C.A. West J Med (1990) 153:323–325.

McCusick, V. et al. Mendelian Inheritance in May, 11th ed., Johns Hopkins University Press (Baltimore, 1994) pp. 1882–1887.

Report of the Joint World Health Organization/HH Foundation/French HH Association Meeting, 1993.

Cartwright, Trans Assoc Am Phys (1978) 91:273–281.

Lipinski, M. et al. Tissue Antigens (1978) 11:471–474.

Simon, M. et al. Am J Hum Genet (1987) 41:89–105.

Jazwinska, E.C. et al. Am J Hum Genet (1993) 53:242–257.

Jazwinska, E.C. et al. Am J Hum Genet (1995) 56:428–433.

Worwood, M. et al. Brit J Hematol. (1994) 86:833–846.

Summers, K.M. et al Am J Hum Genet (1989) 45:41–48.

Gyapay, G. et al. Nature Genetics (1994) 7:246–339.

Stone, C. et al. Hum Molec Genet (1994) 3:2043–2046.

Primary Examiner—Stephanie W. Zitomer
Assistant Examiner—Cheryl Liljestrand
Attorney, Agent, or Firm—Townsend and Townsend and Crew LLP

[57] ABSTRACT

New genetic markers for the presence of a mutation in the common hereditary hemochromatosis (HH) gene are disclosed. The multiplicity of markers permits definition of genotypes characteristic of carriers and homozygotes containing this mutation in their genomic DNA.

16 Claims, 7 Drawing Sheets

1260 bp around the polymorphism 1884.

```
AGCTATACTA AAATTCTTCA GCTTTCATTT TTGGGCCCAT GCTTAGTATT GTTAAAAACT
TATTTGTAGA ACATTCATGT TTTTGATATA AATTGTATGA ATACAATTTA TTTCAAAACA
TTTCCTTTGG CTGAAAACGC CATAGCCTTA AGAAAACTTT ATTAAAAAGA CAAAGTCTTT
CAGACATTTG CAAAAATGCA TCAGTAATAA CCCTAATTCA TCACACTGGA TAAAATTTCT
ATCTGGTTAA GATTTCATCA CTTCAAGCTA AAGCGGAAGA AGGAGGTTTT TATATTGATA
TTGGAAAAGT CCTTGATTGT ATTGGATGCC ATTATTCTTA TCTCTAAACA TGAACTGATG
TCACCATTTC TTTATATCAG TCTCAGTTTT GATAACAAAT TGACTCTCTT AAACTTCTTA
AGCAGATTGA TAATTCATGC ACTTCCTTGT ATCCAGTGAC TCTAATCTTA AACAAATGGA
ACATAAAATA CTGAACCAAT TAGCAAAATG AACTGTTTCT TAAACGTTTA TAACAATCTA
TGGATCTTAT TGTGCCTAAA TAGATTAATC ATTTTAATTT TTTTAAAAAT TTAAAATTTC
TCTAAAGTTT TCTTTTGCTT TCTAGATACA CAAATTACAC ACACACACAC ACACACACAC
ACAAACACAC ACACAGTGGC AATTAAATAT TCGTGCCTTG AAAAGTGAGA AAGGATACAG
ATGTCCTTCT GCCTAGTAGA CCTGTTTATG AGAGGTCCTG TAGACTCCCT GTACTCACTT
GACTCCCAAA TTCATTACCT CTATCAACCC AAATATGCTC CTTTTCCTTC TGTGTATCTA
CTTCATTAAA CATCTGTGCA ATCAGCCAGA CACAAACTTG CAGACCCCGC CTCACCACTC
TCCTGCCTCT TATCTGATAA ATCTCCCAGT GCCGCAAATT CTCCCTCTAG CCCGGCTTGT
TCATCTGTAC ACTTGCCTTT ATTACAGCTC TCATACCATA GCAGATCACC ACTGCTTTTC
TCCTAGATTA CTGCAGCCAT CTCCTGTTTG TCTCTCATTT TCCAGTATCA CTCTCTTCTA
ATTTGCTGCA GCTGGAGTTA GGTTCTAAAT TCCAAATTCA TTCATGTATC TACTTTAAAT
AACTCAGTAC TTCTTTTTTG TTTGTTTGTT TTTCATAATG ACAAAACTCC TTAACATGAG
CTACAAGATC ATGCATATTC TGGTCCCTAT TCCTTAACTA GTCAGAGTGA ATGTCATTCC
```

FIG. 1A 1260 bp around polymorphism 19D9.

```
GTAATAAAAT TATTTAGGGT TTTGGATTGT GTCAAAGCCC TATTCAGCAA TGTCTACTTG
AAAATTTCAT TGAAAAAGTA ACTTAAATAA AGTAGCTATT TGAAGGGCTC AGTAGGATAG
AACCCTTGTC CTTAGCATGA ATCATAGTGA GAAGACACTT TTGAATATGT TTGTTTTTCT
TCTATTACCA GGAAAACATA GGATCATAAA TCACAATTAT TCCATATGTT TTAGAAATTA
ATCATGTGTA TCTTTGCACA AGCACCATAA TGCTTGTGTG TATAAATGAG TATGCATGCA
TACTTGTAAA CACACAGCTT TCATACTCGC TTTTATTATT GTCACTTTTA ACAGCCCCTT
ACATGAAATT TATATTTAAA AAGTGAGAAC ATTTATATTC ATTCTGATGT ATTCAGACAC
TTGTATTAAA TTCTTAGCTC TACTATTTGT GGTCTGTTTG ATAATGTTTC CTAATCTATC
AAATGAAAGG ATTCTGAATT GATCATTTGT TTTCAAATGT ATATTCATGT TAGAATCTCA
CAAGGAGCTT TTTCAACAAA ATATTTCCAG ACTTTCAAAA ACTCACAATC ACTGTGGTTG
GAACTTGAAA CAAACATATG TGTGTCTGTG TGTGTATATA TATATATATA CACACACACA
GACACACATA TATATATCTT TATGTAATTT TAATGCAGCT GATCAGTGAA ACAGTGTTAA
GCTCAAAAAT TTTAATGATG TCATTTTCCA TGTCTTCACT AACCTTCTCT CTTCTCCTTT
TCTCTCTTTT CCTTCCTACC AAATTTTTC CTACCTATTT TTACTCTCCA TTTTCTCACT
CCCCTTTAAC TCATTTCCAT TACACAAACT ACTATTACAC AAACTACTCA TATAATTTTT
CCTCATCTTA TCTTCCCAAA GCATAACTTC TGTCAGTCAA TCCACAGTAC TAAAGCATTG
ATTTATGGTT CTGTTGGATT TTAATTAGCT GTGGTCAATT TGGAAAGGAG GAGAAAAAAT
GATTTGACAT GTCAGATACA ACATGTTATA CAGATTAAAT TTCAGCTGTA ATCTAACTAG
TCATCAGCAT TTTATTCAGG GCTTTACAAT AAGTATTCCC AAGTTCTGCC TCTGTAGGTT
TGTATTGGGT AGGTAGGAAT ATTTAAATGA ATTTGAAGT TTCACTTCAA GAATTATTTA
TTTCTATTAA ATAAGTAAAG AAGCAGTCTC AAGAGCAGTC ACTGTCACTG TGTTTTCTAG
```

FIG. 1B

Aproximately 1kb of sequence around the polymorphism 1A2.

TTGTTCTGTG CCTTAGCTTT ATTTCCAAAG TTCCAGAAAA GACAAGTCAC AGATCGGGAG
AAAATATTTG CAAAACATAT ATACCATGAC CCATGAGGCC CCTCCTCTGC CACTGCCACT
GCCACTGCCA CTGAGATGGT GTATCTCACT TCCTACCTAT TACCTTCCCT CATGAGCAAC
ACCTCCCTTA GTGCCAAGGA CATTAAGAAG ATCCTGGACA GAGTAGGCAT GGAGGCAACT
GATGACTGGC TAAACAAGGT TATCAGTGAG CTGAATGGAA AAAATATTGA AGATATCATT
GCCCAAGGTA TTGGTGAGCT TGCCAGTGTG CCTGCTGGTG GGGCTGTGGC CCTCTCTGCT
TCTCTGGGCT CTGCAGGTCC TGCTGCTGGT TCTACCCCTG CTGCAGAAGA AAGATGACAA
GAAGGAGGAG TCATCTGAAG AGTTGGCCTG TTCAATTAAA TTCCTGGTGT CCTACAAACA
AGCCTTTTC ACATTAAAAA AAAACAAACA AACCAGTGTG TGTGTGTGTG TGTGTGTGTG
TGTGTGTAAT AGAGGCTTTG TATTCAAAAT ATACAAAGAA CTCCAAAGTT CAACAATAAG
AAAACATGTA AACCAATTAA AAAATGGGCA AAATATCTGA ACTGACACCT TAACAAAGAA
GACATGCAAA TGGCAAATAA GCATGTAAAA AGATAGTCAA TGTCATTTTT TATTAGGAAA
TTGCAAACCA GAAAACAGGG AGATACCACT ACATTCTTAT TAGAATGGAC TAAAATCTAA
AAAATCGACA ATACCAATTG CTAGCAAGGA TGCGGAGTGG CAGAAAGTCT CATTTATTTC
TTGTGAGATG CAGAAGAGTA CATCAATTTC CTGATCACTG CAATTCATTC CATGACCCAC
ATAGATATTT TTCTCCCCAT ATGTTAGGGA AGCAGATCTC TCATGGTCTT CATGGACTTC
TCTTTCTGAG TGGAAATTCA CAAGGGTATC TTCTAGTTAT CTATTCCAAT CTCCCCCACC
CTCATCTAGC ATCTTGAAGG GTCTTGGTTG

FIG. 1C

Aproximately 1380bp around polymorphism 1E4.

```
CTGTAAAGTT ACCATTTTTC CTTTTTAAAT TAATAATTAT CTTGAGAGGG AATATTTTGA
GATTATGAAA ATATTCTGTT TCTCATCATA TTTTTGCTAC TTATATTGAT GTTCATCAGT
GATTCTTGCC TGCAACAATT ATTTCTGTAG CATCTATTTT CTATTTCTAT TGCTAATTCT
ACATTTATTA ATTGGAATTC TACTGTAAAG AAGAGCTGTT ATTTTTCCCC CATTTGTTAT
TTGTTCAGTC ATTTATTTAA ACTCATATAG ACTTATGGGT ATTTGTTTTA TTCTATTGTT
TGTAGTCCCA ATACTATCAT TATTTAATTT ACTGCTAAAA TTGTCCTAGA TTTGGCCTTT
GGGAGCTCCT TCAAGTTGAC TCATGTATCT TTTTAACATG CCCCATCACT ATTTGAGAAC
TTCTATACTC TGTGTCACCA CCAGCTGTTC TAGGGTCATC TTGGACTTTT ACTTCCCCAG
CCCTGGAATT ACTAATTTTT CTAAGGATCC TTGGTTCCTT TTACTGGAAA TATATTTAGA
AATCAAGTTC TAGGCACCAG GTGTGTTCAT TGCTACTGAT TTGTTATTGC TTCCAGACTC
TCTCAGTGAA CAGAGCTTAC AAATAGAGTG TGTGTGTGTG TATATATATA TATATATATA
TATATATATA TACTGACATA TACATACACA TACATTTTTA TTTATATACC TAGCTGTGTG
TGTGTATGTG TGTGTGTGTG ACCACAGTTC ATACTAATGC CTCTGATTCC AATCCAAATA
CCACATAGTA TTTGCATAAA CTCCCTCCAT TCCTTATTTG TACCTTCTTT GTTGAACAGT
GGGAAATTTG GCTCTCATTA TCCATAATAT ATTTACTTAT TTTCTCAATT CTAATACACA
AATAGCTTTA GAATTGCTAA TCCACACTCT TGGGAATAAC CATTTTACTA ACTAGAGTAC
AATATTTCTG TACAGTTCTT TTTGCTTTTA TCCTTAGATG AGTCTATCCT TAGCAAAATA
GTCAAGATAC TCTTTTTCCC AAAGTTAATT AGGTTAGTTT TTTTTCCTTC CTTACCCTCT
TTAACTTGGT TTTGTTGCTC ATTTGTAATA CAGGTGGGTT AATTTATTAT TCTCTGTATT
TCTTTTGGGT ACCTCCCATT CCGGTTGACT TTAGTTATTT ATTTAAATTG GAATATGTGA
AGCATTACTA TGGCTATAAA AGTTAGAACA CACAAAATGT TATATGTACT TAGAAAAGTG
TCACTCCCCC TCAGCCTTTC CATTCCACTA ATTCTCCCAT TTTTTTATAC TCTATTCCAA
ATCACCACCT CCTCCAACCC TGTGGGTAAC TAATCTCATT AGTTCTGGT TTATCATTCC
```

FIG. 1D 1260 bp around the polymorphism 24E2.

```
CCCAGAATTG GCCTTCCAAT GCACCAAAAA CTGTAATCAC AACATTTTCA AGGGTTGTCA
CACTTTACAT CAATGTTTGT ACAATTCAGT GTAAACTAGA CCTTTCTGAT CCAGAAATCA
TCTCTTCAGT AATACACACA CGCACACACA CATACATACA TACACACACA CACATAGAAA
CCAAGATGTA AAGGGAGCTT TTGAGAGGTT GCTTGCAAGG GTGTTAATAA AAAAAAAAGG
AATTCTCAAA TTATAGGCCT TTTAAAGACT TCAATTTTAC ATAGCTTATA ATTTAATTCT
CTCCAAATTG CTTTATTATT ACTATTCTTA GAAAACTAT TATAGTGATC TTCAAATAAA
ATGTCGACAG AGAACTATAT CTGTTTTCTA CTGCCTAAAT ATATTCATTG CACAAGTCTT
AAGAACTGAT CTTTTATGAA CTCTCAAAAT AGCATATCCT TGAAATCTTT AAGGTCTCAA
ACATCTTAGC ACTAGTCTGT ATACATCGGG AAGAGACTTA GACTTCTCTG AAACCAGAAT
AAAAGCCAGA AACAAAACAT TTGATACAT ATACACATGT CCTCATCCTT ACACACACAC
ACACACACAC ACACACACAC ACAAACTCCA TGGCACAAAT TATTTTTCAG ACAATTGTAG
ATCTAACAGA AGTATCCAAA ACCTTGTCTT AATTTTCTCT ATAAGTTTAA CAGCCCTAGC
TTAAATTTTA ACACTATTCG CACATCAACA CAATACTAAA ATCCACAACA ATTCTGCACT
CCCCAGTTTT ACTTAGATCT TCTGTTGTTT CTGTACTTCC CACTTCTAAG TTGAAGTGTC
CTATTCCATC TATCAAATAA AGTTGTAGCT ACATTTAGA CTGAAATCGA ATGCCTGCTT
TTGACCTTTT AAAATGATTC CTCTACTGTA TATATTATCT CTCTCCTTTT AACCTCGAAA
GCACTTATAG GGGCCGGGCG CGGTGGCTTA TGCCTGTAAT CCTAGCACTT TGGGAGGCCG
AGGCAGGCGG ATTGCCTGAG GTTAGGAGTT CAAGACCAGC CTGGGCAACA ATGGTGAAAC
CCTGTCTCTA CTAAAATACA AAAATTAGCC AGGCATGACC GCGTGCGCCT GTAGTCCCAG
CTACTTGGGA GGCTGAGGCA GGAGAATCGC TTGAACCCAG GAGGCGGAGG TTGCGGTGAG
CTGAGGTCAC GCCATTGCAC TCCAGCCTGG GCAACAGAGC GAGACTCCAT CTCAAAAAAA
```

FIG. 1E

Aproximately 1kb of sequence around the polymorphism 2B8.

AGCTTTCTTT TGCCATTAAC AAGTAATAAC AAGGATTGAG TAGTAACAAG AAATTCTTCC
TTCCACATAA AGCAAACACC TCATGGTCTT GCTTTATCTC CTTTCTTCTT GATTCTCTAT
CATCTCAGAA AATCAAACAT GAATGTCATT AAGCTCAATT ATATAAATGA TTCAAAATGT
GCAGAATCCA CGGTTGATTA TGGTGTTGGA TATACTAAAG CTGGATAATT AAACAATTTA
TTTTGGCTCT CATTCAAGCA TTTGGCACTA TAAAAGCATA TTTGAACTTT CTAGAAAAAA
ATAAGTGCTT CTTCAGCAAG ACTTCGAAGA TCTTTCGTTT CATATATTGC TGAGGACCTA
CTAAGTCCTT CTAAGATCTT TCTTTTCATA CATCGTTGAG GACCTATTAA ATAACTGTGA
TAGAAACTGG TATGAGAACA AAAATGCCTA GTGTCTACAT TCACGAACAA TATTTTGGAG
GCTTCTGGTG ATGAATGCTT GATTTAGAAG GACTTGAAAG GAATACAAGT GATTGTCAAC
TCAGGAGGAA TATTACATTT TTTACACTCT TGCTTTCTTT CTTTCTTTCC TCTTTCTTTC
TTTCTTTCTT TCTTTCTTTC TTTCTTTCCT CTTTCTTCTC TCTCTCTCTC TCTCTCTCTC
TCTCTCTCTG ACAGGGTCTT GCTCTGTCAC CCAGACTGAG TGCAGTGGCA CAAACACGGC
TCACTGTAGC TTCAAATTCC CAGGCTCAAG CAATCCTCCC ACCTCAGCCT TCTGAGTAGC
TGGGACTGTA GGCATGCACC ACCATGCCTG GCTAACTTTT TAAATTTTTC GTACAGATGG
GGGTCTCACT ATGTTGCTCA GGCTAGTCTC AAACTCCTGG ACTCAAGCAA TACTCCCACC
TCCCAAAGTG CTGGGATTAC AGGCAGGAGC CACTGCTCCT AGCCCCTATT TTCTTGACCT
AGCTAAACCA TTGAATTCCC CCATCTCATT AAATGCCTCT TCAGCCTGCA ATGCCAAAAC
ATTCCTATAT TTGCTAGGTC TAACAACATA TATAGAAGAT GGGTCAAAAT ACAATCCCAA
AGTTTAATCA CCCCTTACTA TATTTCTGCA CTCCCCTTCC CTAGCACCTT CTTCATGGCC
TCTTTAACAT CTTTGTTTCT TAGTGTATAG ATCAGGGGGT TAACACTGGG AGTGACAATT
GTGTAGAAAA GGGTAAGAAA CTTGCCCTGG TCCTGGGAAT AAGTATTTGC TGGCTGGAGG
TACATGTATA TGATTGTACC ATAGAAGAGA GAGACAACAA TTAGATGCGA GCTGCAAGTG

FIG. 1F

| | | | | SEQ ID NO. |
|---|---|---|---|---|
| AG77 | HHp1-A | CACCAAGTACACCAGCTC | POR | HHp1 | 31 |
| AG78 | HHP1-B | ACTCACACGCAAAAAGCC | POR | HHp1 | 32 |
| AG64 | HHp1/3'OLA | p-CTTCCAGAGAAAGAGCCTGT-dig | OLA | HHp1 | 33 |
| AG62 | HHp1/5'OLA-G | bio-TCTTTTCAGAGCCACTCACG | OLA | HHp1 | 34 |
| AG63 | HHp1/5'OLA-A | bio-TCTTTTCAGAGCCACTCACA | OLA | HHp1 | 35 |
| AG110 | HHp19-A | CTAACAATCAATAAAATACACTC | POR | HHp19 | 36 |
| AG111 | HHp19-B | ATACCCAAGAAAAATTCAAAAG | POR | HHp19 | 37 |
| AG143 | HHp19/3'OLA | p-AGACAATTAAGAATGTGAGGT-dig | OLA | HHp19 | 38 |
| AG144 | HHp19/5'OLA-A | bio-ATATATCTATAATCTATATTCTTA | OLA | HHp19 | 39 |
| AG145 | HHp19/5'OLA-G | bio-ATATATCTATAATCTATATTCTTG | OLA | HHp19 | 40 |
| AG165 | HHp29-A | CTTCCTCTCTTCCATATC | POR | HHp26-29 | 41 |
| AG166 | HHp29-B | CCCTCTATATTAGGTTTTC | POR | HHp26-29 | 42 |
| AG190 | HHp29/3'OLA | p-TTTTAAAAATGTTTAATCTTTGTG-dig | OLA | HHp29 | 43 |
| AG191 | HHp29/5'OLA-T | bio-TTGGGATTTTATAGATTTAT | OLA | HHp29 | 44 |
| AG192 | HHp29/5'OLA-G | bio-TTGGGATTTTATAGATTTTAG | OLA | HHp29 | 45 |

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
( A ) LENGTH: 18 base pairs
( B ) TYPE: nucleic acid
( C ) STRANDEDNESS: single (D) TOPOLOGY: linear (xi) SEQUENCE DESCRIPTION: SEQ ID NO:1:

AGTCATCTGA AGAGTTGG                                                                                     18

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:2:

GCATGTCTTC TTTGTTAAGG                                                                                   20

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:3:

AATCAAGTTC TAGGCACC                                                                                     18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:4:

GAATGGAGGG AGTTTATG                                                                                     18

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:5:

CTGTTTACAT CGGGAAGAGA CTTAG                                                                             25

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:6:

CGAATAGTGT TAAAATTTAA GCTAGGGCTG                                                                        30

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear ( x i ) SEQUENCE DESCRIPTION: SEQ ID NO:7:

CTATGGATCT TATTGTGCCT                                                                          20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TACAGGGAGT CTACAGGACC                                                                          20

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AGACTTTCAA AAACTCACAA TCAC                                                                     24

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GATAGAACAT TAGCTTAGAC ATGG                                                                     24

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GAAGGACTTG AAAGGAATAC                                                                          20

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GGAATTTGAA GCTACAGTG                                                                           19

( 2 ) INFORMATION FOR SEQ ID NO:13:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
TTTGGGTTTA TTGCCTGCCT CC                                                22
```

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
AACAATGCCC TTCCTTTC                                                     18
```

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
AACCCAGAAT CACATCTAGT GAGG                                              24
```

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
TGATGCATAT GGCCTTTTCT TTCTC                                             25
```

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
ATGCTGTTAT TTTTCACTT TTTCCTG                                            27
```

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
AGTACTCTGT TGCAGTGAGA GATG                                              24
```

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
ATAGACACTG ACATCATCCC TACC                                              24
```

( 2 ) INFORMATION FOR SEQ ID NO:20:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GTTTCTCTC CAGGACAAAT TTACC        25

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

TTTACTTCTG TTGCCTTAAT G        21

( 2 ) INFORMATION FOR SEQ ID NO:22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

TGAGAGTTTC AGTGAGCC        18

( 2 ) INFORMATION FOR SEQ ID NO:23:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GCAAATCAAG AATGTAATTC CC        22

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

CTTCCAATCC ATAAGCATGG        20

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GCCCTATAAA ATCCTAATTA AC        22

( 2 ) INFORMATION FOR SEQ ID NO:26:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:26:

GAAGGAGAAT TGTAATTCCG   20

( 2 ) INFORMATION FOR SEQ ID NO:27:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:27:

TCTGGGATTC CTGTCCAATG   20

( 2 ) INFORMATION FOR SEQ ID NO:28:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:28:

CCTGACATAT AGTAGGCACT C   21

( 2 ) INFORMATION FOR SEQ ID NO:29:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:29:

TGCTCCATTG CACTCC   16

( 2 ) INFORMATION FOR SEQ ID NO:30:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:30:

CTGATCACCC TCGATATTT AC   22

( 2 ) INFORMATION FOR SEQ ID NO:31:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:31:

CACCAAGTAC ACCAGCTC   18

( 2 ) INFORMATION FOR SEQ ID NO:32:

( i ) SEQUENCE CHARACTERISTICS:

(A) LENGTH: 18 base pairs
(B) TYPE: nucleic acid
(C) STRANDEDNESS: single
(D) TOPOLOGY: linear (x i) SEQUENCE DESCRIPTION: SEQ ID NO:32:

ACTCACACGC AAAAAGCC                                                                 18

(2) INFORMATION FOR SEQ ID NO:33:

(i) SEQUENCE CHARACTERISTICS:
(A) LENGTH: 20 base pairs
(B) TYPE: nucleic acid
(C) STRANDEDNESS: single
(D) TOPOLOGY: linear (i x) FEATURE:
(A) NAME/KEY: misc_difference
(B) LOCATION: replace(1, "")
(D) OTHER INFORMATION: /note= "This position is p-C."

(x i) SEQUENCE DESCRIPTION: SEQ ID NO:33:

CTTCCAGAGA AAGAGCCTGT                                                               20

(2) INFORMATION FOR SEQ ID NO:34:

(i) SEQUENCE CHARACTERISTICS:
(A) LENGTH: 20 base pairs
(B) TYPE: nucleic acid
(C) STRANDEDNESS: single
(D) TOPOLOGY: linear (i x) FEATURE:
(A) NAME/KEY: misc_difference
(B) LOCATION: replace(1, "")
(D) OTHER INFORMATION: /note= "This position is bio-T."

(x i) SEQUENCE DESCRIPTION: SEQ ID NO:34:

TCTTTTCAGA GCCACTCACG                                                               20

(2) INFORMATION FOR SEQ ID NO:35:

(i) SEQUENCE CHARACTERISTICS:
(A) LENGTH: 20 base pairs
(B) TYPE: nucleic acid
(C) STRANDEDNESS: single
(D) TOPOLOGY: linear (i x) FEATURE:
(A) NAME/KEY: misc_difference
(B) LOCATION: replace(1, "")
(D) OTHER INFORMATION: /note= "This position is bio-T."

(x i) SEQUENCE DESCRIPTION: SEQ ID NO:35:

TCTTTTCAGA GCCACTCACA                                                               20

(2) INFORMATION FOR SEQ ID NO:36:

(i) SEQUENCE CHARACTERISTICS:
(A) LENGTH: 23 base pairs
(B) TYPE: nucleic acid
(C) STRANDEDNESS: single
(D) TOPOLOGY: linear (x i) SEQUENCE DESCRIPTION: SEQ ID NO:36:

CTAACAATCA ATAAAATACA CTC                                                           23

(2) INFORMATION FOR SEQ ID NO:37:

(i) SEQUENCE CHARACTERISTICS:

(A) LENGTH: 21 base pairs
            (B) TYPE: nucleic acid
            (C) STRANDEDNESS: single
            (D) TOPOLOGY: linear (x i) SEQUENCE DESCRIPTION: SEQ ID NO:37:

ATACCCAAGA AAATTCAAAA G        21

( 2 ) INFORMATION FOR SEQ ID NO:38:

( i ) SEQUENCE CHARACTERISTICS:
            (A) LENGTH: 21 base pairs
            (B) TYPE: nucleic acid
            (C) STRANDEDNESS: single
            (D) TOPOLOGY: linear ( i x ) FEATURE:
            (A) NAME/KEY: misc_difference
            (B) LOCATION: replace(1, "")
            (D) OTHER INFORMATION: /note= "This position is p-A."

(x i) SEQUENCE DESCRIPTION: SEQ ID NO:38:

AGACAATTAA GAATGTGAGG T        21

( 2 ) INFORMATION FOR SEQ ID NO:39:

( i ) SEQUENCE CHARACTERISTICS:
            (A) LENGTH: 25 base pairs
            (B) TYPE: nucleic acid
            (C) STRANDEDNESS: single
            (D) TOPOLOGY: linear ( i x ) FEATURE:
            (A) NAME/KEY: misc_difference
            (B) LOCATION: replace(1, "")
            (D) OTHER INFORMATION: /note= "This position is bio-A."

(x i) SEQUENCE DESCRIPTION: SEQ ID NO:39:

ATATATCTAT AATCTATATT TCTTA        25

( 2 ) INFORMATION FOR SEQ ID NO:40:

( i ) SEQUENCE CHARACTERISTICS:
            (A) LENGTH: 25 base pairs
            (B) TYPE: nucleic acid
            (C) STRANDEDNESS: single
            (D) TOPOLOGY: linear ( i x ) FEATURE:
            (A) NAME/KEY: misc_difference
            (B) LOCATION: replace(1, "")
            (D) OTHER INFORMATION: /note= "This position is bio-A."

(x i) SEQUENCE DESCRIPTION: SEQ ID NO:40:

ATATATCTAT AATCTATATT TCTTG        25

( 2 ) INFORMATION FOR SEQ ID NO:41:

( i ) SEQUENCE CHARACTERISTICS:
            (A) LENGTH: 18 base pairs
            (B) TYPE: nucleic acid
            (C) STRANDEDNESS: single
            (D) TOPOLOGY: linear (x i) SEQUENCE DESCRIPTION: SEQ ID NO:41:

CTTCCTCTCT TCCATATC        18

( 2 ) INFORMATION FOR SEQ ID NO:42:

( i ) SEQUENCE CHARACTERISTICS:

( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:42:

CCCTCTATAT TAGGTTTTC 19

( 2 ) INFORMATION FOR SEQ ID NO:43:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i x ) FEATURE:
( A ) NAME/KEY: misc_difference
( B ) LOCATION: replace(1, "")
( D ) OTHER INFORMATION: /note= "This position is p-T."

( x i ) SEQUENCE DESCRIPTION: SEQ ID NO:43:

TTTTAAAAAA TGTTTAATCT TTGTG 25

( 2 ) INFORMATION FOR SEQ ID NO:44:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i x ) FEATURE:
( A ) NAME/KEY: misc_difference
( B ) LOCATION: replace(1, "")
( D ) OTHER INFORMATION: /note= "This position is bio-T."

( x i ) SEQUENCE DESCRIPTION: SEQ ID NO:44:

TTGGGGATTT TATAGATTTT AT 22

( 2 ) INFORMATION FOR SEQ ID NO:45:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i x ) FEATURE:
( A ) NAME/KEY: misc_difference
( B ) LOCATION: replace(1, "")
( D ) OTHER INFORMATION: /note= "This position is bio-T."

( x i ) SEQUENCE DESCRIPTION: SEQ ID NO:45:

TTGGGGATTT TATAGATTTT AG 22

( 2 ) INFORMATION FOR SEQ ID NO:46:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:46:

TCTTTTCAGA GCCACTCACG CTTCCAGAGA AAGAGCCT 38

( 2 ) INFORMATION FOR SEQ ID NO:47:

( i ) SEQUENCE CHARACTERISTICS:

( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:47:

TCTTTTCAGA GCCACTCACA CTTCCAGAGA AAGAGCCT 38

( 2 ) INFORMATION FOR SEQ ID NO:48:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:48:

ATATATCTAT AATCTATATT TCTTAAGACA ATTAAGAATG 40

( 2 ) INFORMATION FOR SEQ ID NO:49:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:49:

ATATATCTAT AATCTATATT TCTTGAGACA ATTAAGAATG 40

( 2 ) INFORMATION FOR SEQ ID NO:50:

( i ) SEQUENCE CHARACTERISTICS:
( A ) LENGTH: 46 base pairs
( B ) TYPE: nucleic acid
( C ) STRANDEDNESS: single
( D ) TOPOLOGY: linear ( x i ) SEQUENCE DESCRIPTION: SEQ ID NO:50:

TTGGGGATTT TATAGATTTT ATTTTAAAA AATGTTTAAT CTTTGT 46

( 2 ) INFORMATION FOR SEQ ID NO:51:

( i ) SEQUENCE CHARACTERISTICS:
( A ) LENGTH: 46 base pairs
( B ) TYPE: nucleic acid
( C ) STRANDEDNESS: single
( D ) TOPOLOGY: linear ( x i ) SEQUENCE DESCRIPTION: SEQ ID NO:51:

TTGGGGATTT TATAGATTTT AGTTTAAAA AATGTTTAAT CTTTGT 46

( 2 ) INFORMATION FOR SEQ ID NO:52:

( i ) SEQUENCE CHARACTERISTICS:
( A ) LENGTH: 1260 base pairs
( B ) TYPE: nucleic acid
( C ) STRANDEDNESS: single
( D ) TOPOLOGY: linear ( x i ) SEQUENCE DESCRIPTION: SEQ ID NO:52:

AGCTATACTA AAATTCTTCA GCTTTCATTT TTGGGCCCAT GCTTAGTATT GTTAAAAACT 60

TATTTGTAGA ACATTCATGT TTTGATATA AATTGTATGA ATACAATTTA TTTCAAAACA 120

TTTCCTTTGG CTGAAAACGC CATAGCCTTA AGAAACTTT ATTAAAAGA CAAAGTCTTT 180

CAGACATTTG CAAAAATGCA TCAGTAATAA CCCTAATTCA TCACACTGGA TAAAATTTCT 240

| | | | | | | |
|---|---|---|---|---|---|---|
| ATCTGGTTAA | GATTTCATCA | CTTCAAGCTA | AAGCGGAAGA | AGGAGGTTTT | TATATTGATA | 300 |
| TTGGAAAAGT | CCTTGATTGT | ATTGGATGCC | ATTATTCTTA | TCTCTAAACA | TGAACTGATG | 360 |
| TCACCATTTC | TTTATATCAG | TCTCAGTTTT | GATAACAAAT | TGACTCTCTT | AAACTTCTTA | 420 |
| AGCAGATTGA | TAATTCATGC | ACTTCCTTGT | ATCCAGTGAC | TCTAATCTTA | AACAAATGGA | 480 |
| ACATAAAATA | CTGAACCAAT | TAGCAAAATG | AACTGTTTCT | TAAACGTTTA | TAACAATCTA | 540 |
| TGGATCTTAT | TGTGCCTAAA | TAGATTAATC | ATTTTAATTT | TTTTAAAAAT | TTAAAATTTC | 600 |
| TCTAAAGTTT | TCTTTTGCTT | TCTAGATACA | CAAATTACAC | ACACACACAC | ACACACACAC | 660 |
| ACAAACACAC | ACACAGTGGC | AATTAAATAT | TCGTGCCTTG | AAAAGTGAGA | AAGGATACAG | 720 |
| ATGTCCTTCT | GCCTAGTAGA | CCTGTTTATG | AGAGGTCCTG | TAGACTCCCT | GTACTCACTT | 780 |
| GACTCCCAAA | TTCATTACCT | CTATCAACCC | AAATATGCTC | CTTTTCCTTC | TGTGTATCTA | 840 |
| CTTCATTAAA | CATCTGTGCA | ATCAGCCAGA | CACAAACTTG | CAGACCCCGC | CTCACCACTC | 900 |
| TCCTGCCTCT | TATCTGATAA | ATCTCCCAGT | GCCGCAAATT | CTCCCTCTAG | CCCGGCTTGT | 960 |
| TCATCTGTAC | ACTTGCCTTT | ATTACAGCTC | TCATACCATA | GCAGATCACC | ACTGCTTTTC | 1020 |
| TCCTAGATTA | CTGCAGCCAT | CTCCTGTTTG | TCTCTCATTT | TCCAGTATCA | CTCTCTTCTA | 1080 |
| ATTTGCTGCA | GCTGGAGTTA | GGTTCTAAAT | TCCAAATTCA | TTCATGTATC | TACTTTAAAT | 1140 |
| AACTCAGTAC | TTCTTTTTTG | TTTGTTTGTT | TTTCATAATG | ACAAAACTCC | TTAACATGAG | 1200 |
| CTACAAGATC | ATGCATATTC | TGGTCCCTAT | TCCTTAACTA | GTCAGAGTGA | ATGTCATTCC | 1260 |

( 2 ) INFORMATION FOR SEQ ID NO:53:

( i ) SEQUENCE CHARACTERISTICS:
        ( A ) LENGTH: 1260 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

| | | | | | | |
|---|---|---|---|---|---|---|
| GTAATAAAAT | TATTTAGGGT | TTTGGATTGT | GTCAAAGCCC | TATTCAGCAA | TGTCTACTTG | 60 |
| AAAATTTCAT | TGAAAAAGTA | ACTTAAATAA | AGTAGCTATT | TGAAGGGCTC | AGTAGGATAG | 120 |
| AACCCTTGTC | CTTAGCATGA | ATCATAGTGA | GAAGACACTT | TTGAATATGT | TTGTTTTTCT | 180 |
| TCTATTACCA | GGAAAACATA | GGATCATAAA | TCACAATTAT | TCCATATGTT | TTAGAAATTA | 240 |
| ATCATGTGTA | TCTTTGCACA | AGCACCATAA | TGCTTGTGTG | TATAAATGAG | TATGCATGCA | 300 |
| TACTTGTAAA | CACACAGCTT | TCATACTCGC | TTTTATTATT | GTCACTTTTA | ACAGCCCCTT | 360 |
| ACATGAAATT | TATATTTAAA | AAGTGAGAAC | ATTTATATTC | ATTCTGATGT | ATTCAGACAC | 420 |
| TTGTATTAAA | TTCTTAGCTC | TACTATTTGT | GGTCTGTTTG | ATAATGTTTC | CTAATCTATC | 480 |
| AAATGAAAGG | ATTCTGAATT | GATCATTTGT | TTTCAAATGT | ATATTCATGT | TAGAATCTCA | 540 |
| CAAGGAGCTT | TTTCAACAAA | ATATTTCCAG | ACTTTCAAAA | ACTCACAATC | ACTGTGGTTG | 600 |
| GAACTTGAAA | CAAACATATG | TGTGTCTGTG | TGTGTATATA | TATATATATA | CACACACACA | 660 |
| GACACACATA | TATATATCTT | TATGTAATTT | TAATGCAGCT | GATCAGTGAA | ACAGTGTTAA | 720 |
| GCTCAAAAAT | TTTAATGATG | TCATTTTCCA | TGTCTTCACT | AACCTTCTCT | CTTCTCCTTT | 780 |
| TCTCTCTTTT | CCTTCCTACC | AAATTTTTTC | CTACCTATTT | TTACTCTCCA | TTTTCTCACT | 840 |
| CCCCTTTAAC | TCATTTCCAT | TACACAAACT | ACTATTACAC | AAACTACTCA | TATAATTTTT | 900 |
| CCTCATCTTA | TCTTCCCAAA | GCATAACTTC | TGTCAGTCAA | TCCACAGTAC | TAAAGCATTG | 960 |
| ATTTATGGTT | CTGTTGGATT | TTAATTAGCT | GTGGTCAATT | TGGAAGGAG | GAGAAAAAAT | 1020 |
| GATTTGACAT | GTCAGATACA | ACATGTTATA | CAGATTAAAT | TTCAGCTGTA | ATCTAACTAG | 1080 |

| | | | | | |
|---|---|---|---|---|---|
| TCATCAGCAT | TTTATTCAGG | GCTTTACAAT | AAGTATTCCC | AAGTTCTGCC | TCTGTAGGTT | 1140 |
| TGTATTGGGT | AGGTAGGAAT | ATTTAAATGA | ATTTTGAAGT | TTCACTTCAA | GAATTATTTA | 1200 |
| TTTCTATTAA | ATAAGTAAAG | AAGCAGTCTC | AAGAGCAGTC | ACTGTCACTG | TGTTTTCTAG | 1260 |

( 2 ) INFORMATION FOR SEQ ID NO:54:

( i ) SEQUENCE CHARACTERISTICS:
        ( A ) LENGTH: 1050 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

| | | | | | |
|---|---|---|---|---|---|
| TTGTTCTGTG | CCTTAGCTTT | ATTTCCAAAG | TTCCAGAAAA | GACAAGTCAC | AGATCGGGAG | 60 |
| AAAATATTTG | CAAAACATAT | ATACCATGAC | CCATGAGGCC | CTCCTCTGC | CACTGCCACT | 120 |
| GCCACTGCCA | CTGAGATGGT | GTATCTCACT | TCCTACCTAT | TACCTTCCCT | CATGAGCAAC | 180 |
| ACCTCCCTTA | GTGCCAAGGA | CATTAAGAAG | ATCCTGGACA | GAGTAGGCAT | GGAGGCAACT | 240 |
| GATGACTGGC | TAAACAAGGT | TATCAGTGAG | CTGAATGGAA | AAAATATTGA | AGATATCATT | 300 |
| GCCCAAGGTA | TTGGTGAGCT | TGCCAGTGTG | CCTGCTGGTG | GGCTGTGGC | CCTCTCTGCT | 360 |
| TCTCTGGGCT | CTGCAGGTCC | TGCTGCTGGT | TCTACCCCTG | CTGCAGAAGA | AAGATGACAA | 420 |
| GAAGGAGGAG | TCATCTGAAG | AGTTGGCCTG | TTCAATTAAA | TTCCTGGTGT | CCTACAAACA | 480 |
| AAGCCTTTTC | ACATTAAAAA | AAAACAAACA | AACCAGTGTG | TGTGTGTGTG | TGTGTGTGTG | 540 |
| TGTGTGTAAT | AGAGGCTTTG | TATTCAAAAT | ATACAAAGAA | CTCCAAAGTT | CAACAATAAG | 600 |
| AAAACATGTA | AACCAATTAA | AAAATGGGCA | AAATATCTGA | ACTGACACCT | TAACAAAGAA | 660 |
| GACATGCAAA | TGGCAAATAA | GCATGTAAAA | AGATAGTCAA | TGTCATTTTT | TATTAGGAAA | 720 |
| TTGCAAACCA | GAAACAGGG | AGATACCACT | ACATTCTTAT | TAGAATGGAC | TAAAATCTAA | 780 |
| AAAATCGACA | ATACCAATTG | CTAGCAAGGA | TGCGGAGTGG | CAGAAAGTCT | CATTTATTTC | 840 |
| TTGTGAGATG | CAGAAGAGTA | CATCAATTTC | CTGATCACTG | CAATTCATTC | CATGACCCAC | 900 |
| ATAGATATTT | TTCTCCCCAT | ATGTTAGGGA | AGCAGATCTC | TCATGGTCTT | CATGGACTTC | 960 |
| TCTTTCTGAG | TGGAAATTCA | CAAGGGTATC | TTCTAGTTAT | CTATTCCAAT | CTCCCCCACC | 1020 |
| CTCATCTAGC | ATCTTGAAGG | GTCTTGGTTG | | | | 1050 |

( 2 ) INFORMATION FOR SEQ ID NO:55:

( i ) SEQUENCE CHARACTERISTICS:
        ( A ) LENGTH: 1380 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

| | | | | | |
|---|---|---|---|---|---|
| CTGTAAAGTT | ACCATTTTTC | CTTTTTAAAT | TAATAATTAT | CTTGAGAGGG | AATATTTTGA | 60 |
| GATTATGAAA | ATATTCTGTT | TCTCATCATA | TTTTTGCTAC | TTATATTGAT | GTTCATCAGT | 120 |
| GATTCTTGCC | TGCAACAATT | ATTTCTGTAG | CATCTATTTT | CTATTTCTAT | TGCTAATTCT | 180 |
| ACATTTATTA | ATTGGAATTC | TACTGTAAAG | AAGAGCTGTT | ATTTTCCCC | CATTTGTTAT | 240 |
| TTGTTCAGTC | ATTTATTTAA | ACTCATATAG | ACTTATGGGT | ATTTGTTTTA | TTCTATTGTT | 300 |
| TGTAGTCCCA | ATACTATCAT | TATTTAATTT | ACTGCTAAAA | TTGTCCTAGA | TTTGGCCTTT | 360 |
| GGGAGCTCCT | TCAAGTTGAC | TCATGTATCT | TTTTAACATG | CCCCATCACT | ATTTGAGAAC | 420 |
| TTCTATACTC | TGTGTCACCA | CCAGCTGTTC | TAGGGTCATC | TTGGACTTTT | ACTTCCCCAG | 480 |

```
CCCTGGAATT ACTAATTTTT CTAAGGATCC TTGGTTCCTT TTACTGGAAA TATATTTAGA      540
AATCAAGTTC TAGGCACCAG GTGTGTTCAT TGCTACTGAT TTGTTATTGC TTCCAGACTC      600
TCTCAGTGAA CAGAGCTTAC AAATAGAGTG TGTGTGTGTG TATATATATA TATATATATA      660
TATATATATA TACTGACATA TACATACACA TACATTTTTA TTTATATACC TAGCTGTGTG      720
TGTGTATGTG TGTGTGTGTG ACCACAGTTC ATACTAATGC CTCTGATTCC AATCCAAATA      780
CCACATAGTA TTTGCATAAA CTCCCTCCAT TCCTTATTTG TACCTTCTTT GTTGAACAGT      840
GGGAAATTTG GCTCTCATTA TCCATAATAT ATTTACTTAT TTCTCAATT CTAATACACA       900
AATAGCTTTA GAATTGCTAA TCCACACTCT TGGGAATAAC CATTTTACTA ACTAGAGTAC      960
AATATTTCTG TACAGTTCTT TTTGCTTTTA TCCTTAGATG AGTCTATCCT TAGCAAAATA     1020
GTCAAGATAC TCTTTTTCCC AAAGTTAATT AGGTTAGTTT TTTTTCCTTC CTTACCCTCT     1080
TTAACTTGGT TTTGTTGCTC ATTTGTAATA CAGGTGGGTT AATTTATTAT TCTCTGTATT     1140
TCTTTTGGGT ACCTCCCATT CCGGTTGACT TTAGTTATTT ATTTAAATTG GAATATGTGA     1200
AGCATTACTA TGGCTATAAA AGTTAGAACA CACAAAATGT TATATGTACT TAGAAAAGTG     1260
TCACTCCCCC TCAGCCTTTC CATTCCACTA ATTCTCCCAT TTTTTATAC TCTATTCCAA      1320
ATCACCACCT CCTCCAACCC TGTGGGTAAC TAATCTCATT AGTTTCTGGT TTATCATTCC     1380
```

( 2 ) INFORMATION FOR SEQ ID NO:56:

( i ) SEQUENCE CHARACTERISTICS:
        ( A ) LENGTH: 1260 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

```
CCCAGAATTG GCCTTCCAAT GCACCAAAAA CTGTAATCAC AACATTTTCA AGGGTTGTCA       60
CACTTTACAT CAATGTTTGT ACAATTCAGT GTAAACTAGA CCTTTCTGAT CCAGAAATCA      120
TCTCTTCAGT AATACACACA CGCACACACA CATACATACA TACACACACA CACATAGAAA      180
CCAAGATGTA AAGGGAGCTT TGAGAGGTT GCTTGCAAGG GTGTTAATAA AAAAAAAAGG       240
AATTCTCAAA TTATAGGCCT TTTAAAGACT TCAATTTTAC ATAGCTTATA ATTTAATTCT      300
CTCCAAATTG CTTTATTATT ACTATTCTTA GAAAAACTAT TATAGTGATC TTCAAATAAA     360
ATGTCGACAG AGAACTATAT CTGTTTTCTA CTGCCTAAAT ATATTCATTG CACAAGTCTT      420
AAGAACTGAT CTTTTATGAA CTCTCAAAAT AGCATATCCT TGAAATCTTT AAGGTCTCAA      480
ACATCTTAGC ACTAGTCTGT ATACATCGGG AAGAGACTTA GACTTCTCTG AAACCAGAAT      540
AAAAGCCAGA AACAAAACAT TTGATACAT ATACACATGT CCTCATCCTT ACACACACAC       600
ACACACACAC ACACACACAC ACAAACTCCA TGGCACAAAT TATTTTTCAG ACAATTGTAG      660
ATCTAACAGA AGTATCCAAA ACCTTGTCTT AATTTTCTCT ATAAGTTTAA CAGCCCTAGC      720
TTAAATTTTA ACACTATTCG CACATCAACA CAATACTAAA ATCCACAACA ATTCTGCACT      780
CCCCAGTTTT ACTTAGATCT TCTGTTGTTT CTGTACTTCC CACTTCTAAG TTGAAGTGTC      840
CTATTCCATC TATCAAATAA AGTTGTAGCT ACATTTAGA CTGAAATCGA ATGCCTGCTT       900
TTGACCTTTT AAAATGATTC CTCTACTGTA TATATTATCT CTCTCCTTTT AACCTCGAAA      960
GCACTTATAG GGGCCGGGCG CGGTGGCTTA TGCCTGTAAT CCTAGCACTT TGGGAGGCCG     1020
AGGCAGGCGG ATTGCCTGAG GTTAGGAGTT CAAGACCAGC CTGGGCAACA ATGGTGAAAC     1080
CCTGTCTCTA CTAAAATACA AAAATTAGCC AGGCATGACC GCGTGCGCCT GTAGTCCCAG     1140
```

-continued

```
CTACTTGGGA GGCTGAGGCA GGAGAATCGC TTGAACCCAG GAGGCGGAGG TTGCGGTGAG      1200
CTGAGGTCAC GCCATTGCAC TCCAGCCTGG GCAACAGAGC GAGACTCCAT CTCAAAAAAA      1260
```

( 2 ) INFORMATION FOR SEQ ID NO:57:

( i ) SEQUENCE CHARACTERISTICS:
        ( A ) LENGTH: 1320 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

```
AGCTTTCTTT TGCCATTAAC AAGTAATAAC AAGGATTGAG TAGTAACAAG AAATTCTTCC        60
TTCCACATAA AGCAAACACC TCATGGTCTT GCTTTATCTC CTTTCTTCTT GATTCTCTAT       120
CATCTCAGAA AATCAAACAT GAATGTCATT AAGCTCAATT ATATAAATGA TTCAAAATGT       180
GCAGAATCCA CGGTTGATTA TGGTGTTGGA TATACTAAAG CTGGATAATT AAACAATTTA       240
TTTTGGCTCT CATTCAAGCA TTTGGCACTA TAAAAGCATA TTTGAACTTT CTAGAAAAAA       300
ATAAGTGCTT CTTCAGCAAG ACTTCGAAGA TCTTTCGTTT CATATATTGC TGAGGACCTA       360
CTAAGTCCTT CTAAGATCTT TCTTTTCATA CATCGTTGAG GACCTATTAA ATAACTGTGA       420
TAGAAACTGG TATGAGAACA AAAATGCCTA GTGTCTACAT TCACGAACAA TATTTGGAG        480
GCTTCTGGTG ATGAATGCTT GATTAGAAG GACTTGAAAG GAATACAAGT GATTGTCAAC        540
TCAGGAGGAA TATTACATTT TTTACACTCT TGCTTTCTTT CTTTCTTTCC TCTTTCTTTC       600
TTTCTTTCTT TCTTTCTTTC TTTCTTTCCT CTTTCTTCTC TCTCTCTCTC TCTCTCTCTC       660
TCTCTCTCTG ACAGGGTCTT GCTCTGTCAC CCAGACTGAG TGCAGTGGCA CAAACACGGC       720
TCACTGTAGC TTCAAATTCC CAGGCTCAAG CAATCCTCCC ACCTCAGCCT TCTGAGTAGC       780
TGGGACTGTA GGCATGCACC ACCATGCCTG GCTAACTTTT TAAATTTTTC GTACAGATGG       840
GGGTCTCACT ATGTTGCTCA GGCTAGTCTC AAACTCCTGG ACTCAAGCAA TACTCCCACC       900
TCCCAAAGTG CTGGGATTAC AGGCAGGAGC CACTGCTCCT AGCCCCTATT TTCTTGACCT       960
AGCTAAACCA TTGAATTCCC CCATCTCATT AAATGCCTCT TCAGCCTGCA ATGCCAAAAC      1020
ATTCCTATAT TTGCTAGGTC TAACAACATA TATAGAAGAT GGGTCAAAAT ACAATCCCAA      1080
AGTTAATCA CCCCTTACTA TATTTCTGCA CTCCCCTTCC CTAGCACCTT CTTCATGGCC       1140
TCTTTAACAT CTTTGTTTCT TAGTGTATAG ATCAGGGGGT TAACACTGGG AGTGACAATT      1200
GTGTAGAAAA GGGTAAGAAA CTTGCCCTGG TCCTGGGAAT AAGTATTTGC TGGCTGGAGG      1260
TACATGTATA TGATTGTACC ATAGAAGAGA GAGACAACAA TTAGATGCGA GCTGCAAGTG      1320
```

METHOD TO DIAGNOSE HEREDITARY HEMOCHROMATOSIS

TECHNICAL FIELD

The invention relates to genetic tests for subjects carrying one or two copies of a mutated gene associated with hereditary hemochromatosis. More specifically, the invention concerns utilization of new markers associated with a common mutation in this gene which indicate the presence or absence of the mutation.

BACKGROUND ART

Hereditary hemochromatosis (HH) is an inherited disorder of iron metabolism wherein the body accumulates excess iron. In symptomatic individuals, this excess iron leads to deleterious effects by being deposited in a variety of organs leading to their failure, and resulting in cirrhosis, diabetes, sterility, and other serious illnesses. Neither the precise physiological mechanism of iron overaccumulation nor the gene which is defective in this disease is known.

HH is inherited as a recessive trait; heterozygotes are asymptomatic and only homozygotes are affected by the disease. It is estimated that approximately 10% of individuals of Western European descent carry an HH gene mutation and that there are about one million homozygotes in the United States. Although ultimately HH produces debilitating symptoms, the majority of homozygotes have not been diagnosed. Indeed, it has been estimated that no more than 10,000 people in the United States have been diagnosed with this condition. The symptoms are often confused with those of other conditions, and the severe effects of the disease often do not appear immediately. It would be desirable to provide a method to identify persons who are ultimately destined to become symptomatic in order to intervene in time to prevent excessive tissue damage. One reason for the lack of early diagnosis is the inadequacy of presently available diagnostic methods to ascertain which individuals are at risk.

Although blood iron parameters can be used as a screening tool, a confirmed diagnosis often employs HLA typing, which is tedious, nonspecific, and expensive and/or liver biopsy which is undesirably invasive and costly. Accordingly, others have attempted to develop inexpensive and noninvasive diagnostics both for detection of homozygotes having existing disease, in that presymptomatic detection would guide intervention to prevent organ damage, and for identification of carriers. The need for such diagnostics is documented for example, in Finch, C. A. *West J Med* (1990) 153:323–325; McCusick, V. et al. *Mendelian Inheritance in Man* 11th ed., Johns Hopkins University Press (Baltimore, 1994) pp. 1882–1887; Report of the Joint World Health Organization/HH Foundation/French HH Association Meeting, 1993.

Although the gene carrying the mutation associated with HH is at present unknown, genetic linkage studies in HH families have shown that the gene responsible in Caucasians resides on chromosome 6 near the HLA region at 6p2.13 (Cartwright, *Trans Assoc Am Phys* (1978) 91:273–281; Lipinski, M. et al. *Tissue Antigens* (1978) 11:471–474). Within this gene a single mutation gives rise to the majority of disease-causing chromosomes present in the population today. This is referred to herein as the "common" or "ancestral" or "common ancestral" mutation. These terms are used interchangeably. It appears that 80–90% of all HH patients carry at least one copy of a common ancestral mutation which carries with it specific forms of certain markers close to this ancestral HH gene. These markers are, as a first approximation, in the allelic form in which they were present at the time the HH mutation occurred. See, for example, Simon, M. et al. *Am J Hum Genet* (1987) 41:89–105; Jazwinska, E. C. et al. *Am J Hum Genet* (1993) 53:242–257; Jazwinska, E. C. et al. *Am J Hum Genet* (1995) 56:428–433; Worwood, M. et al. *Brit J Hematol* (1994) 86:833–846; Summers, K. M. et al. *Am J Hum Genet* (1989) 45:41–48.

Although each of such markers is putatively useful in identifying individuals carrying this defective HH gene, of course, crossing over events have, over time, separated some of the ancestral alleles from the relevant genetic locus that is responsible for HH. Therefore, no single marker is currently specific enough to identify individuals carrying the ancestral HH mutation.

Several markers at the approximate location of the gene associated with HH have been described. Gyapay, G. et al. *Nature Genetics* (1994) 7:246–339 describe the markers D6S306 and D6S258 which have been demonstrated hereinbelow to be in the immediate region of the HH gene. These markers consist of microsatellite regions containing $(CA)_n$ repeats of various lengths. Worwood, M. et al. *Brit J Hematol* (1994) 86:833–846 (supra) describes an allele at D6S265 and Jazwinska, E. C. et al. *Am J Hum Genet* (1993) 53:242–257 (supra) describes D6S105 as associated with an HH-specific genotype. Stone, C. et al. *Hum Molec Genet* (1994) 3:2043–2046 describes an additional HH-associated allele at D6S1001. As described hereinbelow, 10 previously undiscovered microsatellite markers and the relevant allele associated with the ancestral HH gene defect have now been found permitting the detection of genotypes with very high probabilities of being associated with the presence of the common HH mutated gene. In addition, 3 single base-pair polymorphisms associated with the HH gene have been identified, which can be included in additional diagnostic genotypes. The diagnostic genotypes described below as associated with HH are rare in the general population, consistent with the frequency of the HH gene mutation. However, they are present in a large majority of individuals affected by HH. Accordingly, the presence or absence of these genotypes can be used as a rapid, inexpensive and noninvasive method to assess an individual for the presence or absence of the common version of the defective HH gene.

DISCLOSURE OF THE INVENTION

The invention is directed to a convenient method to assess individuals for the presence or absence, or the likelihood of said presence or absence, of a common HH-associated mutation using genetic techniques that are readily applied noninvasively. Only a sample containing the subject's cells containing genomic DNA from the subject to be tested is required. The present invention includes materials and kits useful in conducting the genetic tests. The allelic variants at specific locations close to the HH gene are marked by distinctive lengths of microsatellite repeats or by specific single base-pair differences in DNA sequence (referred to herein as a "base-pair polymorphism").

Thus, in one aspect, the invention is directed to a method to determine the likelihood of the presence or absence of a hereditary hemochromatosis (HH) gene mutation in an individual, which method comprises obtaining genomic DNA from the cells of said individual and assessing said DNA for the presence or absence of a genotype defined by at least one nonoptional marker comprising the following microsatellite repeat alleles: 19D9:205; 18B4:235; 1A2:239; 1E4:271; 24E2:245; 2B8:206; 3321-1:197; 4073-1:182; 4440-1:180; and 4440-2:139. In the notation employed for the microsatellite repeat alleles, the number subsequent to the colon indicates the number of nucleotides in the HH-associated allele between and including the flanking primers when the primers are those illustrated herein. The absence of this genotype indicates the likelihood of the absence of the HH gene mutation in the genome of said individual. The presence of this genotype indicates the likelihood of the presence of this HH gene mutation in the genome of said individual.

While the presence of only one of these alleles indicates an increased likelihood for the presence of the common ancestral genetic HH defect, the likelihood is further enhanced by the presence of multiple alleles among these nonoptional markers. Thus, the genotypes to be determined preferably include at least two, more preferably at least three, and more preferably still, at least four, preferably more than four, of these alleles. In addition, the statistical certainty of the results is enhanced by combining the information concerning the presence or absence of one or more of these nonoptional alleles with the information concerning the presence or absence of diagnostic alleles known in the art, including D6S258:199, D6S265:122, D6S105:124, D6S306:238, D6S464:206; and D6S1001:180. The predictive power of such disease-associated alleles when measured in human genomic DNA can be quantified. An example of a computerized method for this is given in Terwilliger, J. D. *Am J Hum Genet* (1995) 56:777–787.

In addition, HHP-1, HHP-19, and HHP-29 (described below) base-pair polymorphisms have been established; the presence of the HH-associated allele of one of these base-pair polymorphisms especially in combination with any HH-mutation-associated microsatellite repeat allele indicates the presence of the common HH mutant gene.

Thus, in another aspect, the invention is directed to a method to determine the presence or absence of the common hereditary hemochromatosis (HH) gene mutation in an individual, which method comprises obtaining genomic DNA from the individual; and assessing the DNA for the presence or absence of the HH-associated allele of the base-pair polymorphism designated herein at HHP-1, HHP-19, or HHP-29; wherein the absence of the HH-associated allele indicates the likelihood of the absence of the ancestral HH gene mutation in the genome of the individual and the presence of the HH-associated allele indicates the likelihood of the presence of the HH gene mutation in the genome of the individual. Preferably, the method also includes determining a genotype which is a combination of the base-pair allele with an HH-associated microsatellite repeat allele.

The invention is further directed to DNA primer pairs for PCR amplification that flank the microsatellite repeat alleles and that flank the base-pair polymorphism markers useful in the method of the invention and to kits containing these primer pairs. The invention is also directed to primers permitting determination of base-pair polymorphisms by oligonucleotide ligation assay (OLA) or by alternative methods. The invention is also directed to use of the nucleotide sequence information around the microsatellite repeats to design additional primer pairs for amplification. Applicants have provided extensive sequence information approximately 500 bp in either direction of the markers 18B4, 19D9, 1A2, 1E4, 24E2, and 2B8. The availability of this sequence information provides additional opportunities for the design of primers for amplification of the relevant portion of DNA.

Accordingly, the invention is also directed to primers designed on the basis of this sequence information and to a computer-readable medium having recorded thereon the nucleotide sequences set forth in FIG. 1A–1F described below or fragments thereof. The claimed fragments are those that do not coincide with nucleotide sequences presently available in computer-readable form.

BRIEF DESCRIPTION OF THE DRAWINGS

FIGS. 1A–1F show sequence information concerning the portions of the genome surrounding several markers of the invention. FIG. 1A (SEQ ID NO:52) shows 1260 bp around 18B4; FIG. 1B (SEQ ID NO:53) shows 1260 bp around 19D9; FIG. 1C (SEQ ID NO:54) shows 1 kb around 1A2; FIG. 1D (SEQ ID NO:55) shows 1380 bp around 1E4; FIG. 1E (SEQ ID NO:56) shows 1260 bp around 24E2; and FIG. 1F (SEQ ID NO:57) shows approximately 1 kb around 2B8. The location of the microsatellite repeated sequence itself is underlined in these figures.

FIG. 2 (SEQ ID NO:31 through SEQ ID NO:45) shows the primers used for amplification and OLA determination of the base-pair polymorphisms of the invention.

MODES OF CARRYING OUT THE INVENTION

Ten new markers which are of variant length microsatellite repeats associated with the ancestral mutation in the gene associated with hereditary hemochromatosis have been found and the allelic forms associated with the HH genetic defect have been characterized. In general, the markers reside on chromosome 6 in the neighborhood of the locus which is associated with the defective genotype and exhibit a multiplicity of allelic variations characterized by a variation in the number of nucleotides present in the intervening sequence between flanking sequences conserved in all subjects. The intervening nucleotide sequences consist essentially of di-, tri- and tetranucleotide repeats, most commonly the dinucleotide $(CA)_n$. As is generally known in the art, this type of repeat is known as a "microsatellite" repeat. The microsatellite repeat regions which characterize the markers of the present invention may be simple microsatellite repeats containing only one type of repeated sequence or may be compound. In addition to $(CA)_n$, $(CT)_n$ and other repeated sequences are found. These repeat sequences generically, are designated "microsatellite repeats" herein. As shown hereinbelow, the flanking sequences conserved with respect to each marker are interrupted by intervening nucleotide sequences ranging in number from about 150 to about 300 bases. Generally, the size of each allele differs within the context of a single marker by 2–4 bases from the next closest allele.

As used herein, "marker" refers either to a base-pair polymorphism or to a microsatellite region wherein varying numbers of $(CA)_n$ or other microsatellite repeats are flanked by conserved regions; advantage can be taken of the conserved regions flanking either the base-pair polymorphism or the microsatellite repeat to construct primers for amplifying the relevant DNA portions. In some cases, two sets of PCR primers will be required: one to amplify the general region of the DNA of interest and the other to perform OLA determination of the base-pair polymorphisms. When the microsatellite regions are amplified using the primers set forth herein, representing conserved regions at either end of the repeats intervening sequences of varying lengths result. In the case of each marker, one of the alleles found in the tested population has a higher frequency in individuals known to be affected by HH than in the general population. Each individual marker cannot be completely determinative, since any particular allele associated with HH is also present in at least some normal individuals or chromosomes. However, the presence of the HH-associated allelic form of even one marker indicates an enhanced probability that the subject carries the mutation. By using multiple markers, at least two, preferably at least three, and more preferably at least four, or a greater multiplicity of such alleles to determine a characteristic genotype, this problem is reduced to the extent that substantial predictive power is obtained. The frequency of the occurrence of the characteristic genotype combination of the alleles most commonly encountered in HH-affected individuals has so far reduced to zero in normal subjects; as more individuals are tested, small numbers in the normal population will be found eventually to share some of these genotypes. This is to be expected since approximately one in fifteen individuals is a carrier of the common ancestral mutation and is clinically normal and will remain so.

To standardize the notation, the markers which are microsatellite repeat alleles are denoted by the marker name followed by a colon and the number of nucleotides in the allele found at a higher frequency in HH subjects. Thus, the notation 1A2:239 indicates that the marker bracketed by SEQ ID NO:1 and SEQ ID NO:2 described below has 239 nucleotides which represents the sum of the nucleotides intervening between the two identified primer sequences in the HH genotype plus the nucleotides included in the relevant primers exemplified below, i.e., SEQ ID NO:1 and SEQ ID NO:2. Similarly, 24E2:245 reflects 245 nucleotides between and including the two primers identified as SEQ ID NO:5 and SEQ ID NO:6 in the HH genotype. The location of the intervening nucleotides is shown for six of the repeat markers as an underlined sequence in FIGS 1A–1F.

Shown in FIG. 1A–1F are nucleotide sequences about 500 bp either side of six of the markers described herein. Each portion of the figure shows approximately 1 kb sequence surrounding each polymorphism; FIG. 1A shows marker 18B4; FIG. 1B shows 19D9; FIG. 1C shows 1A2; FIG. 1D shows 1E4; FIG. 1E shows 24E2; and FIG. 1F shows 2B8. These sequences are of sufficient length that it is convenient to provide them in computer-readable medium. The medium would include those known in the art such as floppy disks, hard disks, random access memory (RAM), read only memory (ROM), and CD-ROM. The invention is also directed to computer-readable media having recorded thereon the nucleotide sequence depicted with respect to each marker as set forth in FIG. 1 or a portion of each such sequence wherein said portion is novel—i.e., does not currently exist in computer-readable form.

In addition to the microsatellite repeat markers described above, three single base-pair polymorphisms have been found in which one allele is present in high proportion on chromosomes of affected individuals. These base-pair polymorphisms designated HHP-1, HHP-19 and HHP-29, were discovered in the course of sequencing the relevant portion of chromosome 6 derived from affected as compared to unaffected individuals. HHP-1 is about 80,000 base pairs centromere-proximal to the marker D6S105; HHP-19 is about 110,000 base pairs centromere-proximal to the marker D6S105. HHP-29 is about 185,000 base pairs centromere-proximal to the marker D6S105. The precise nature of these base-pair polymorphisms is set forth in the examples hereinbelow. The presence of one allele, especially in combination with any one of the characteristic allelic variants among the microsatellite repeat markers characterized herein or characterized in the prior art indicates the presence of the common HH mutation.

To perform the diagnostic test, a suitable genomic DNA-containing sample from a subject is obtained and the DNA extracted using conventional techniques. DNA can be prepared, for example, simply by boiling the sample in SDS. Most typically, a blood sample, a buccal swab, a hair follicle preparation or a nasal aspirate is used as a source of cells to provide the DNA. The extracted DNA is then subjected to amplification, for example, using the polymerase chain reaction (PCR) according to standard procedures. Sequential amplification is conducted with various pairs of primers and the amplified DNA is recovered after each amplification, or, in the alternative, the DNA sample can be divided into aliquots and each aliquot amplified separately if sufficient DNA is available. The size of the insert of the amplified marker which is a microsatellite repeat is then determined using gel electrophoresis. See Weber and May *Am J Hum Genet* (1989) 44:388–339; Davies, J. et al. *Nature* (1994) 371:130–136. The presence or absence of the single basepair polymorphism is determined by conventional methods including manual and automated fluorescent DNA sequencing, primer extension methods (Nikiforov, T. T. et al. *Nucl Acids Res* (1994) 22:4167–4175); oligonucleotide ligation assay (OLA) (Nickerson, D. A. et al. *Proc Natl Acad Sci USA* (1990) 87:8923–8927); allele-specific PCR methods (Rust, S. et al. *Nucl Acids Res* (1993) 6:3623–3629); RNase mismatch cleavage, single strand conformation polymorphism (SSCP), denaturing gradient gel electrophoresis (DGGE) and the like.

As will further be described in Example 1, one genotype associated with HH is defined by the following alleles 19D9:205; 18B4:235; 1A2:239; D6S306:238; 1E4:271; 24E2:245; additional alleles that may be included are 2B8:206 and D6S258:199. The absence of this genotype indicates the absence of the ancestral HH gene mutation in the genome of said individual and the presence of said genotype indicates the presence of said HH gene mutation.

In addition to the genotype described above, genotypes characterized by the presence of the allele associated with the HHP-1, the HHP-19 or HHP-29 single base-pair polymorphism in combination with any of the HH-associated allelic variants among the microsatellite repeat markers also characterizes an individual whose genome contains the common HH mutation. If desired, the particular allele associated with the common HH mutation can be designated in a manner analogous to the notation used in connection with the microsatellite repeat markers hereinabove. Thus, the HH-associated alleles for the herein base-pair polymorphisms are HHP-1:A, HHP-19:G, and HHP-29:G. (See Example 4.)

The alleles associated with the single base-pair polymorphisms HHP-1, HHP-19 and HHP-29 have, to date, been observed to be in complete linkage disequilibrium. Thus, the determination that one of these alleles is present or absent specifies the presence or absence of the other. For example, an individual who is homozygous for the HHP-1:A allele is also homozygous for the HHP-19:G and the HHP-29:G alleles.

As will be evident from the above description, individual chromosomes are not necessarily isolated, the particular set of markers associated with a single chromosome can be, but need not be, determined in determining genotypes. Strictly speaking the presence of alleles associated with the common HH mutation should accompany it on the same chromosome. However, the presence of the diagnostic genotype per se is sufficient to indicate the likelihood that the subject carries the common HH mutation even if the chromosomes are not separated in the analysis.

It is apparent, however, that the various genotypes can distinguish between heterozygous carriers and individuals homozygous with respect to the ancestral HH mutation. That is, the presence of more than one genotype can be detected in a single individual even though total DNA is sampled.

The diagnostic methods described below have additional advantages. Although the prior art methods for identification of the presence of the genetic mutation associated with HH are invasive, current medical practice requires investigation of immediate relatives to discover any previously unsuspected cases so that preventive phlebotomy can be initiated (Bothwell, T. H. et al. in *The Metabolic Basis of Inherited Disease*, McGraw Hill, New York, 1995, pp. 2237–2269; Edwards, C. Q. et al. *New Engl J Med* (1993) 328:1616–1620). The methods described in the present invention will be capable of detecting other cases with high accuracy in this family context, even in the event that HH is caused by a nonancestral mutation in this family. This is true because other family members who are affected will carry the same genotype as the affected member (even if these genotypes are not any of the ancestral types listed herein). Thus, these markers will still identify other family members homozygous for the HH gene.

The presence of the HH genotype also has predictive power with respect to certain therapeutic regimes where it is understood that the effectiveness of these regimes is related to the HH genotype. For example, it has been disclosed that the potential for hemochromatosis interferes with the effectiveness of interferon treatment of hepatitis C (Bacon, B. *Abstracts of the Fifth Conference of the International Association for the Study of Disorders of Iron Metabolism* (1995) 15–16. Thus, knowledge of the status of the genotype of the subject with respect to the HH mutation provides guidance in designing therapeutic protocols for conditions affected by disorders of iron metabolism, particularly liver conditions. As the correlations between treatment regimens and iron metabolism continue to become established, the diagnostic methods of the invention provide a useful tool in designing therapeutic protocols consistent with the presence or absence of the common HH mutation.

The following examples are intended to illustrate but not to limit the invention.

EXAMPLE 1

Identification of Markers for HH

Clones containing the relevant sequences were retrieved in a genome walking strategy beginning with the previously described markers D6S306, D6S105 and D6S258. Standard chromosome-walking techniques are described in Sambrook, J. et al. *Molecular Cloning—A Laboratory Manual*, 2nd Ed., Cold Spring Harbor Laboratory Press, New York (1989) and in Dracopoli, H. et al. eds. *Current Protocols in Human Genetics*, J. Wiley & Sons, New York (1994).

The DNA sequence of the human genome in the region of the HH mutated gene was determined. A genomic 3 kb clone library was prepared by sonication of cosmid and phage P1 clones. The sonicated genomic DNA was endrepaired, BstXI adapters were added and the fragments were ligated into pOT2. Resulting clones were subjected to transposon-mediated directed DNA sequencing. See Strathman, et al. *Proc Natl Acad Sci USA* (1991) 88:1247–1250.

As a result of determining the sequence of some of the DNA in this region, the presence of 10 previously unknown microsatellite repeat elements (consisting of repeating di-, tri- and tetranucleotide repeats, most commonly the dinucleotide $(CA)_n$) was noted. The length of these repeats is typically polymorphic in the human population and thus different lengths represent different alleles which are inherited in a Mendelian fashion. This permits them to be used as genetic markers (Weber, J. et al. *Am J Hum Genet* (1989) 44:388–396).

Since the genomic sequence surrounding the repeats was thus available, PCR primers that flank the repeats and represent conserved sequences can be designed. Table 1 shows the names of these sequence repeat markers and the corresponding DNA sequences of the flanking PCR primers.

TABLE 1

Markers in the HH Region on Chromosome 6p2.1

| Marker Name | Primer Sequences 5'→3' | SEQ ID NO |
|---|---|---|
| 1A2 | AGTCATCTGAAGAGTTGG | 1 |
| | GCATGTCTTCTTTGTTAAGG | 2 |
| 1E4 | AATCAAGTTCTAGGCACC | 3 |
| | GAATGGAGGGAGTTTATG | 4 |
| 24E2 | CTGTTTACATCGGGAAGAGACTTAG | 5 |
| | CGAATAGTGTTAAAATTTAAGCTAGGGCTG | 6 |
| 18B4 | CTATGGATCTTATTGTGCCT | 7 |
| | TACAGGGAGTCTACAGGACC | 8 |
| 19D9 | AGACTTTCAAAAACTCACAATCAC | 9 |
| | GATAGAACATTAGCTTAGACATGG | 10 |
| 2B8 | GAAGGACTTGAAAGGAATAC | 11 |
| | GGAATTTGAAGCTACAGTG | 12 |
| 3321-1 | TTTGGGTTTATTGCCTGCCTCC | 13 |
| | AACAATGCCCTTCCTTTC | 14 |
| 4073-1 | AACCCAGAATCACATCTAGTGAGG | 15 |
| | TGATGCATATGGCCTTTTCTTTCTC | 16 |
| 4440-1 | ATGCTGTTATTTTTTCACTTTTTCCTG | 17 |
| | AGTACTCTGTTGCAGTGAGAGATG | 18 |
| 4440-2 | ATAGACACTGACATCATCCCTACC | 19 |
| | GTTTTCTCTCCAGGACAAATTTACC | 20 |
| D6S306 | TTTACTTCTGTTGCCTTAATG | 21 |
| | TGAGAGTTTCAGTGAGCC | 22 |
| D6S258 | GCAAATCAAGAATGTAATTCCC | 23 |
| | CTTCCAATCCATAAGCATGG | 24 |
| D6S105 | GCCCTATAAAATCCTAATTAAC | 25 |
| | GAAGGAGAATTGTAATTCCG | 26 |
| D6S1001 | TCTGGGATTCCTGTCCAATG | 27 |
| | CCTGACATATAGTAGGCACTC | 28 |
| D6S464 | TGCTCCATTGCACTCC | 29 |
| | CTGATCACCCTCGATATTTTAC | 30 |

As shown in Table 1, ten new markers were identified; with respect to the prior art markers D6S306 D6S258, D6S105, D6S1001, and D6S464, the appropriate primer oligonucleotides are also determined. As will be shown in Example 2, the alleles associated with HH for both the ten new markers and four known markers have also been determined.

EXAMPLE 2

Association of Alleles with the Presence of HH

Total genomic DNA from families represented in the CEPH collection (Dausset, J. et al. *Genomics* (1990) 6:575–577) was used as a substrate for amplification with the 14 pairs of primers representing the markers in Table 1. None of the individuals in the CEPH collection is known to have HH; thus, the results in these individuals indicate the frequencies of the various alleles in the normal population. These results are shown as the "% Normals" in Table 2.

TABLE 2

Allele Distribution for HH Markers

| Marker Name | Allele Size (base pr.) | % Normals | % HH |
|---|---|---|---|
| | 237 | 2 | 0 |
| | 239 | 46 | 77 |
| 1A2 | 241 | 35 | 21 |
| | 243 | 16 | 3 |

TABLE 2-continued

Allele Distribution for HH Markers

| Marker Name | Allele Size (base pr.) | % Normals | % HH |
|---|---|---|---|
| 1E4 | 257 | 1 | 0 |
|  | 261 | 1 | 0 |
|  | 265 | 4 | 0 |
|  | 267 | 10 | 7 |
|  | 269 | 31 | 13 |
|  | 271 | 28 | 70 |
|  | 273 | 9 | 5 |
|  | 275 | 9 | 0 |
|  | 277 | 3 | 0 |
|  | 279 | 1 | 0 |
|  | 281 | 1 | 0 |
|  | 283 | 3 | 5 |
|  | 285 | 1 | 0 |
|  | 287 | 1 | 0 |
| 24E2 | 251 | 2 | 0 |
|  | 235 | 6 | 5 |
|  | 237 | 1 | 0 |
|  | 239 | 1 | 0 |
|  | 241 | 3 | 0 |
|  | 243 | 18 | 9 |
|  | 245 | 63 | 82 |
|  | 247 | 9 | 4 |
| 18B4 | 231 | 1 | 0 |
|  | 233 | 23 | 12 |
|  | 235 | 42 | 78 |
|  | 237 | 25 | 10 |
|  | 239 | 8 | 0 |
| 19D9 | 183 | 1 | 0 |
|  | 185 | 1 | 0 |
|  | 199 | 9 | 1 |
|  | 201 | 2 | 0 |
|  | 203 | 15 | 12 |
|  | 205 | 63 | 87 |
| 2B8 | 198 | 0 | 0 |
|  | 202 | 0 | 4 |
|  | 204 | 4 | 1 |
|  | 206 | 14 | 67 |
|  | 210 | 27 | 10 |
|  | 214 | 11 | 6 |
|  | 216 | 2 | 0 |
|  | 218 | 3 | 1 |
|  | 220 | 5 | 8 |
|  | 226 | 2 | 0 |
|  | 228 | 10 | 0 |
|  | 230 | 4 | 0 |
|  | 232 | 3 | 3 |
|  | 234 | 3 | 0 |
| 3321-1 | 195 | 21 | 12 |
|  | 197 | 71 | 81 |
|  | 199 | 8 | 8 |
|  | 201 | 1 | 0 |
| 4073-1 | 180 | 3 | 2 |
|  | 182 | 49 | 82 |
|  | 184 | 12 | 5 |
|  | 186 | 21 | 5 |
|  | 188 | 7 | 4 |
|  | 190 | 3 | 1 |
|  | 192 | 1 | 0 |
|  | 212 | 1 | 0 |
|  | 238 | 1 | 0 |
| 4440-1 | 176 | 10 | 13 |
|  | 178 | 47 | 25 |
|  | 180 | 38 | 61 |
|  | 182 | 3 | 1 |
| 4440-2 | 139 | 58 | 82 |
|  | 141 | 2 | 0 |
|  | 143 | 9 | 4 |
|  | 145 | 0 | 1 |
|  | 149 | 7 | 1 |
|  | 151 | 1 | 0 |
|  | 155 | 5 | 3 |
|  | 157 | 4 | 4 |
|  | 159 | 8 | 4 |
|  | 161 | 2 | 1 |
|  | 163 | 3 | 0 |
|  | 165 | 1 | 0 |
|  | 167 | 1 | 0 |
| D6S464 | 202 | 4 | 1 |
|  | 204 | 6 | 3 |
|  | 206 | 52 | 84 |
|  | 208 | 2 | 0 |
|  | 210 | 8 | 3 |
|  | 214 | 2 | 0 |
|  | 216 | 13 | 7 |
|  | 218 | 2 | 0 |
|  | 220 | 2 | 1 |
|  | 222 | 2 | 0 |
|  | 224 | 8 | 1 |
|  | 230 | 4 | 0 |
|  | 234 | 2 | 3 |
| D6S306 | 238 | 54 | 74 |
|  | 240 | 22 | 12 |
|  | 244 | 11 | 10 |
|  | 246 | 6 | 0 |
|  | 248 | 2 | 0 |
| D6S258 | 189 | 11 | 5 |
|  | 193 | 2 | 0 |
|  | 197 | 30 | 12 |
|  | 199 | 33 | 72 |
|  | 201 | 6 | 7 |
|  | 203 | 2 | 2 |
|  | 205 | 6 | 1 |
|  | 207 | 6 | 0 |
| D6S105 | 116 | 2 | 0 |
|  | 122 | 2 | 1 |
|  | 124 | 13 | 64 |
|  | 126 | 8 | 3 |
|  | 128 | 39 | 17 |
|  | 130 | 14 | 5 |
|  | 132 | 11 | 8 |
|  | 134 | 5 | 3 |
|  | 136 | 3 | 0 |
|  | 138 | 3 | 0 |
| D6S1001 | 176 | 18 | 8 |
|  | 178 | 12 | 4 |
|  | 180 | 40 | 79 |
|  | 182 | 11 | 4 |
|  | 184 | 4 | 0 |
|  | 186 | 1 | 0 |
|  | 188 | 2 | 0 |
|  | 190 | 5 | 4 |
|  | 192 | 6 | 1 |
|  | 196 | 1 | 0 |
|  | 200 | 2 | 0 |

With respect to HH, the haplotypes for many of the single chromosomes were obtained from the DNA of cell hybrid lines, each of which contained a single chromosome 6 from an HH-affected individual (Shay, J. W. *Techniques in Somatic Cell Genetics*, Plenem, New York, 1982). These results are shown as "% HH" in Table 2. For each marker, generally one allele was more common in HH chromosomes as compared to normal individuals.

EXAMPLE 3

Determination of Haplotypes Associated with HH

Table 3 shows a compilation of haplotypes assembled from the alleles most commonly occurring in HH chromosomes. Haplotype A assembles six of the ten markers; haplotypes B and C expand the assembly with one additional marker each and haplotype D adds two additional markers for a total of eight.

TABLE 3

6p Marker Haplotype Associations with HH

| Markers | D6S258 | 19D9 | 18B4 | 1A2 | 2B8 | D6S306 | 1E4 | 24E2 |
|---|---|---|---|---|---|---|---|---|
| Haplotype A | | 205 | 235 | 239 | | 238 | 271 | 245 |
| Haplotype B | | 205 | 235 | 239 | 206 | 238 | 271 | 245 |
| Haplotype C | 199 | 205 | 235 | 239 | | 238 | 271 | 245 |
| Haplotype D | 199 | 205 | 235 | 239 | 206 | 238 | 271 | 245 |

Table 4 shows the distribution of these haplotypes as determined in 74 hemochromatosis chromosomes and 56 chromosomes from unaffected individuals. Inheritance patterns could be used to associate the haplotypes with particular chromosomes in the CEPH individuals and HH individuals.

TABLE 4

Frequency of Haplotypes in Affected and Unaffected: (%)

| | Individuals | | Chromosomes | |
|---|---|---|---|---|
| | Affected | Unaffected | Affected | Unaffected |
| A | 89 | 0 | 68 | 0 |
| B | 86 | 0 | 58 | 0 |
| C | 84 | 0 | 61 | 0 |
| D | 81 | 0 | 51 | 0 |

Table 4 clearly shows that none of the haplotypes A-D occurs in unaffected individuals or in unaffected chromosomes tested to date. A very high percentage of individuals affected by HH contains haplotype A and significant numbers contain B-D. Indeed, these haplotypes are present on a majority of chromosomes from HH-affected individuals.

EXAMPLE 4

Single Base-Pair Polymorphisms

In the course of sequencing the HH region of genomic DNA prepared as described in Example 1, and by comparing the sequences obtained for DNA from affected as compared to unaffected individuals, three single base-pair polymorphisms were found and designated HHP-1, HHP-19 and HHP-29 as follows:

HHP-1
Unaffected sequence:
TCTTTTCAGAGCCACTCACGCTTCCA-GAGAAAGAGCCT (SEQ ID NO:46)
Affected sequence:
TCTTTTCAGAGCCACTCACACTTCCA-GAGAAAGAGCCT (SEQ ID NO:47)

HHP-19
Unaffected sequence:
ATATATCTATAATCTATATTTCTTAAGA-CAATTAAGAATG SEQ ID NO:48)
Affected sequence:
ATATATCTATAATCTATATTTCTTGAGA-CAATTAAGAATG (SEQ ID NO:49)

HHP-29
Unaffected sequence:
TTGGGGATTTTATAGATTTTATTTT-TAAAAAATGTTTAATCTTTGT (SEQ ID NO:50)
Affected sequence:
TTGGGGATTTTATAGATTTTAGTTT-TAAAAAATGTTTAATCTTTGT (SEQ ID NO:51)

The presence or absence of these single basepair sequence differences can, of course, be determined in the same DNA samples as those which provide information on the $(CA)_n$ repeat alleles by use of the appropriate primers for amplification and sequencing. FIG. 2 shows the sequences of primers used for amplification and sequencing of the above three base-pair polymorphisms. The amplification primers for HHP-1 are labeled AG77 and AG78; the amplification primers for HHP-19 are labeled AG110 and AG111; and the amplification primers for HHP-29 are labeled AG165 and AG166. The primers used in the sequence determination by OLA are designated, for HHP-1, AG64, AG62 and AG63; for HHP-19, AG143, AG144 and AG145; and for HHP-29 are designated AG190, AG191 and AG192. As indicated in the sequences shown, "bio" indicates biotin coupling; "dig" indicates coupled digoxygenin.

Table 5 shows the frequency of these point mutations in affected and unaffected chromosomes:

TABLE 5

Frequencies of Alleles as % of Chromosomes Tested

| | | Affected Chromosomes | Random Chromosomes |
|---|---|---|---|
| HHP-1 | A | 64% | 6% |
| | G | 36% | 94% |
| HHP-19 | G | 64% | 6% |
| | A | 36% | 94% |
| HHP-29 | G | 64% | 6% |
| | T | 36% | 94% |

The allele in HHP-1:A occurs in 64% of the affected chromosomes; its occurrence at 6% in random chromosomes approximates the estimated frequency of the common HH mutation in the population. As noted hereinabove, according to the results obtained to date, the presence of HHP-1:A is associated with the presence of HHP-19:G and HHP-29:G.

We claim:

1. A method to determine the presence or absence of common hereditary hemochromatosis (HH) in an individual which comprises:

(a) obtaining genomic DNA from said individual;

(b) amplifying a HH-associated allele selected from the group consisting of: HHP-1A, HHP-19G and HHP-29G; and (c) determining whether said individual is heterozygous or homozygous for a base pair polymorphism in said HH-associated allele, wherein homozygosity for any one or all of said alleles is indicative of HH in the individual and absence of homozygosity for any one or all said alleles is indicative of the absence of HH in the individual.

2. The method of claim 1 which further comprises:

determining the presence or absence of at least one HH-associated microsatellite marker in said individual using a primer pair selected from the group consisting of:

SEQ ID Nos. 1 and 2; SEQ ID NOs. 3 and 4; SEQ ID NOs. 5 and 6; SEQ ID NOs. 7 and 8; SEQ ID NOs. 9 and 10; SEQ ID NOs. 11 and 12; SEQ ID NOs. 13 and 14; SEQ ID NOs. 15 and 16; SEQ ID NOs. 17 and 18; SEQ ID NOs. 19 and 20; SEQ ID NOs. 21 and 22; SEQ ID NOs. 23 and 24; SEQ ID NOs. 25 and 26; SEQ ID NOs. 27 and 28; and SEQ ID NOs. 29 and 30;

wherein the presence of said HH-associated allele in combination with at least one microsatellite marker indicates the likely presence of HH in the individual and absence of said HH-associated allele and said microsatellite marker indicates the likely absence of HH in the individual.

3. A set of primers for determining the presence or absence of a hereditary hemochromatosis (HH)-associated allele used in an oligonucleotide ligation assay (OLA) selected from the group consisting of:

SEQ ID NOs. 33–35; SEQ ID NOs. 38–40; and SEQ ID NOs. 43–45.

4. A kit for the detection of the presence or absence of an HH-associated allele comprising at least one primer set of claim 3.

5. A method to determine the likelihood of the presence or absence of common hereditary hemochromatosis (HH) in an individual comprising the steps of:

(a) obtaining genomic DNA from said individual;

(b) amplifying a HH-associated microsatellite marker with a primer pair selected from the group consisting of: SEQ ID Nos. 1 and 2; SEQ ID NOs. 3 and 4; SEQ ID NOs. 5 and 6; SEQ ID NOs. 7 and 8; SEQ ID NOs. 9 and 10; SEQ ID NOs. 11 and 12; SEQ ID NOs. 13 and 14; SEQ ID NOs. 15 and 16; SEQ ID NOs. 17 and 18; and SEQ ID NOs. 19 and 20; wherein said amplifying further comprises the optional step of amplifying said DNA with a primer pair selected from the group consisting of: SEQ ID NOs. 21 and 22; SEQ ID NOs. 23 and 24; SEQ ID NOs. 25 and 26; SEQ ID NOs. 27 and 28; and SEQ ID NOs. 29 and 30;

(c) determining the presence or absence of said microsatellite marker, wherein the presence of said microsatellite markers is indicative of the likely presence of HH in the individual and absence of said microsatellite marker is indicative of the likely absence of HH in the individual.

6. The method of claim 5 wherein said method tests at least two of said markers.

7. The method of claim 6 wherein said method tests at least three of said markers.

8. The method of claim 7 wherein said method tests at least four of said markers.

9. The method of claim 5 wherein said genomic DNA is prepared from a sample of blood or buccal swab from said individual.

10. The method of claim 5 which further comprises the amplification of a microsatellite marker using a pair of DNA primers selected from the group consisting of: SEQ ID NOs. 21 and 22; SEQ ID NOs. 23 and 24; SEQ ID NOs. 25 and 26; SEQ ID NOs. 27 and 28; and SEQ ID NOs. 29 and 30.

11. A pair of DNA primers of about 18 nucleotides in length wherein said primer pairs specifically amplify a Common Hereditary Hemochromatosis (HH) associated microsatellite marker selected from the group consisting of: SEQ ID NO. 52; SEQ ID NO. 53; SEQ ID NO. 54; SEQ ID NO. 55; SEQ ID NO. 56; and SEQ ID NO. 57.

12. A DNA primer pair for amplification of a microsatellite marker associated with Common Hereditary Hemochromatosis (HH) wherein the sequences of said primers are selected from the group consisting of: SEQ ID NOs. 7 and 8; SEQ ID NOs. 9 and 10; SEQ ID NOs. 1 and 2; SEQ ID NOs. 3 and 4; SEQ ID NOs. 5 and 6; SEQ ID NOs. 11 and 12; SEQ ID NOs. 13 and 14; SEQ ID NOs. 15 and 16; SEQ ID NOs. 17 and 18; and SEQ ID NOs. 19 and 20.

13. A kit for the detection of the presence or absence of an hereditary hemochromatosis (HH)-associated microsatellite marker in an individual comprising:

(a) at least one pair of DNA primers of about 18 nucleotides in length wherein said primer pairs specifically amplify said (HH)-associated microsatellite marker selected from the group consisting of:

SEQ ID NO 52; SEQ ID NO 53; SEQ ID NO 54; SEQ ID NO 55; SEQ ID NO 56; and SEQ ID NO 57; and optionally (b) a primer pair selected from the group consisting of: SEQ ID NOs. 7 and 8; SEQ ID NOs. 9 and 10; SEQ ID NOs. 1 and 2; SEQ ID NOs. 3 and 4; SEQ ID NOs. 5 and 6; SEQ ID NOs. 11 and 12; SEQ ID NOs. 13 and 14; SEQ ID NOs. 15 and 16; SEQ ID NOs. 17 and 18; and SEQ ID NOs. 19 and 20.

14. The kit of claim 13 which further comprises a pair of primers selected from the group consisting of: SEQ ID NOs. 21 and 22; SEQ ID NOs. 23 and 24; SEQ ID NOs. 25 and 26; SEQ ID NOs. 27 and 28; and SEQ ID NOs. 29 and 30.

15. A method to identify a potential reduced responsiveness of a subject to interferon treatment for hepatitis C, which method comprises determining the presence or absence of a marker for the common hereditary hemochromatosis gene in said subject according to the method of claim 1, wherein the presence of one of the HH markers indicates a probable reduced responsiveness to said interferon treatment.

16. A method to identify a potential reduced responsiveness of a subject to interferon treatment for hepatitis C, which method comprises determining the presence or absence of a marker for the common hereditary hemochromatosis gene in said subject according to the method of claim 5, wherein the presence of one of the HH markers indicates probable reduced responsiveness to said interferon treatment.

* * * * *